United States Patent [19]

Galliani et al.

[11] Patent Number: 5,219,872
[45] Date of Patent: Jun. 15, 1993

[54] COMPOUNDS OF 1,2,5,6-TETRAHYDROPYRIDIN-3-CARBOXALDEHYDE OXIME WHICH ARE USEFUL AS CHOLINERGIC AGENTS

[75] Inventors: Giulio Galliani; Fernando Barzaghi; Alina Butti, all of Milan; Carla Bonetti, Bergamo; Emilio Toja, Milan, all of Italy

[73] Assignee: Roussel UCLAF, Paris, France

[21] Appl. No.: 19,256

[22] Filed: Feb. 26, 1987

[30] Foreign Application Priority Data

Feb. 27, 1986 [IT] Italy ................ 19565 A/86
Jul. 17, 1986 [IT] Italy ................ 21157 A/86

[51] Int. Cl.$^5$ ................ A61K 31/44; C07D 211/70
[52] U.S. Cl. .................... 514/357; 546/335; 546/338
[58] Field of Search ............... 546/338, 335; 514/357

[56] References Cited

U.S. PATENT DOCUMENTS 3,004,979 10/1961 Druey et al. ............ 546/338
4,710,508 12/1987 Bergmeier et al. ........ 514/357

Primary Examiner—C. Warren Ivy
Assistant Examiner—Zinna N. Davis
Attorney, Agent, or Firm—Stevens, Davis, Miller & Mosher

[57] ABSTRACT

Compounds useful in the treatment of Alzheimer's disease, senile dementia, or memory disorders which have the formula

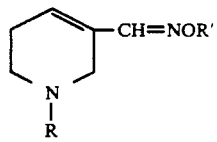

in which R represents a hydrogen atom, a linear, branched or cyclic alkyl radical, saturated or unsaturated, containing up to 8 carbon atoms, possibly substituted by a free or esterified carboxy radical or R represents an aralkyl radical containing up to 10 carbon atoms and R' represents a linear or branched, saturated or unsaturated, alkyl radical, containing up to 8 carbon atoms, a radical —COalk$_1$ or a radical —(CH$_2$)$_2$-N(alk$_2$)$_2$, alk$_1$ and alk$_2$ representing an alkyl radical containing up to 8 carbon atoms, as well as their addition salts with acids. Also compositions containing the same, method of preparation and method of treatment using the same.

14 Claims, No Drawings

COMPOUNDS OF 1,2,5,6-TETRAHYDROPYRIDIN-3-CARBOXALDEHYDE OXIME WHICH ARE USEFUL AS CHOLINERGIC AGENTS

The invention is concerned with new derivatives of 1,2,5,6-tetrahydropyridin-3-carboxaldehyde oxime, their preparation process, their use as medicaments and the compositions containing them.

Derivatives of 1,2,5,6-tetrahydropyridin-3-carboxaldehyde oxime, are already known, such as 1,2,5,6-tetrahydropyridin-3-carboxaldehyde oxime (Chem. Ber. 40, 4685, 1907), 1-methyl-1,2,5,6-tetrahydropyridin-3-carboxaldehyde oxime (Chem. Ber. 40, 4712, 1907), and also 1-ethyl 1,2,5,6-tetrahydropyridin-3-carboxaldehyde oxime (Chem. Ber. 38, 4161, 1905), that is to say, compounds have the general formula:

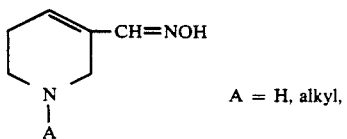

A = H, alkyl,

Certain of these products have even been studied in pharmacology (c.f. Journal of Pharmaceutical Sciences, 1190 Vol. 56, 1967) and interest in them has been very slight, the products being much less active than arecoline.

It has just been discovered unexpectedly, that certain products of a similar chemical structure present very interesting pharmacological properties, greatly superior to that of arecoline, as are shown by the results of pharmacological tests described hereafter.

The subject of the invention is the compounds with the formula (I):

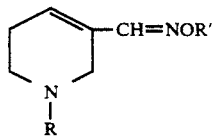

(I)

in which R represents a hydrogen atom, a linear, branched or cyclic alkyl radical, saturated or unsaturated, containing up to 8 carbon atoms, possibly substituted by a free or esterified carboxy radical or R represents an aralkyl radical containing up to 10 carbon atoms and R' represents a linear or branched, saturated or unsaturated, alkyl radical, containing up to 8 carbon atoms, a radical —COalk$_1$ or a radical —(CH$_2$)$_2$-N(alk$_2$)$_2$, alk$_1$ and alk$_2$ representing an alkyl radical containing up to 8 carbon atoms, as well as their addition salts with acids.

Among the addition salts with acids, there can be cited those formed with mineral acids, such as hydrochloric, hydrobromic, sulphuric or phosphoric acids, or with organic acids such as the following: formic, acetic, propionic, benzoic, maleic, fumaric, succinic, tartaric, citric, oxalic, glyoxylic, aspartic, alkanesulphonic, such as methane or ethane sulphonic, arylsulphonic, such as benzene or paratoluene sulphonic.

When R or R' represents a saturated, linear or branched alkyl radical, it is preferred to be a methyl, ethyl, n-propyl, isopropyl, n-butyl, sec-butyl, isobutyl, n-pentyl, tert-butyl, tert-pentyl, neopentyl or n-hexyl radical.

When R or R' represents an unsaturated alkyl radical, it is preferred to be an ethylene radical, such as, for example, a vinyl, allyl, 1,1-dimethylallyl or but-2-enyl radical, or an acetylene radical, such as, for example, an ethynyl or propynyl radical.

When R represents a cyclic alkyl radical, it is preferred to be a cyclopropyl, cyclobutyl, cyclopentyl, cyclohexyl, cyclopropylmethyl, cyclobutylmethyl, cyclopentylmethyl or cyclohexylmethyl radical.

When R represents an aralkyl radical, it is preferred to be a benzyl or phenethyl radical.

When R represents an alkyl radical substituted by an esterified carboxy radical, it is preferred to be a radical substituted by an alkoxycarbonyl group in which the alkoxy radical includes up to 8 carbon atoms, such, for example, as a methoxy, ethoxy, linear or branched propoxy, or linear or branched butoxy radical.

Alk$_1$ and alk$_2$ preferably represent a methyl, ethyl, n-propyl, isopropyl, n-butyl, sec-butyl or isobutyl radical.

The invention has more especially as its subject the compounds with the formula (I) in which R represents a hydrogen atom, as well as their addition salts with acids.

The invention also has more especially as its subject the compounds with the formula (I) in which R represents a saturated or unsaturated alkyl radical containing from 1 to 4 carbon atoms, and particularly a methyl, ethyl, propyl or allyl radical, as well as their addition salts with acids.

Among the preferred compounds of the invention, there can be cited the compounds in which R' represents a methyl radical, as well as their addition salts with acids.

The invention has quite particularly as its subject the compounds of which the preparation is indicated in a detailed manner in the experimental part herein after. Among these compounds, there can be cited as a preferred subject of the invention, the compounds described in the following examples 1,3,7,8 and 10.

The invention compounds present very interesting pharmacological properties and notably an important cholinomimetic activity by oral route with a long duration of activity.

It is well known that the difficulties of learning and of memory in aged persons are connected above with a deficiency in the central cholinergic system, in particular, in senile dementia and Alzheimer's disease.

It is therefore evident that products having a central cholinergic action might be employed in the therapeutic treatment of these diseases. (Bartus, R. I. Science 217, 408, 1982).

It has been shown that arecoline injected by intravenous route has a positive effect on patients having a memory defect (Sitaram N. et al. Science 201, 274, 1978) (Christie J. E. et al Brit. J. Psychiatry, 138, 46, 1981).

A limitation to the therapeutic use of arecoline is connected with the fact that this product has a very weak activity by oral route and a short duration of action.

The products which are the subject of the invention, after administration by oral route, have shown a central cholinomimetic activity up to 1500 times greater than that of arecoline and with a much longer duration of action.

The invention therefore has, as its subject, the invention products as medicaments, useful in particular in the treatment of Alzheimer's disease or of senile dementia and equally in memory disorders.

The invention has more particularly as its subject as medicaments, the compounds of examples 1,3,7,8 and 10.

The usual posology is variable according to the affection concerned, the person treated and the administration route; it can be between 1 mg and 100 mg/day, preferably from 1 to 20 mg/day and for example, between 1 and 15 mg/day in one or more lots for the product of example 3, administered by oral route.

The present invention also has as its subject the pharmaceutical compositions containing as active principle at least one compound with the formula (I). The pharmaceutical compositions of the invention can be solid or liquid and are presented in the pharmaceutical forms currently used in human medecine, such, for example, as plain or sugar-coated tablets, capsules, granules, suppositories, injectable preparations: they are prepared according to the usual methods.

The active principle or principles can be incorporated with the excipients usually employed in these pharmaceutical compositions, such as talc, gum arabic, lactose, starch, magnesium stearate, cocoa butter, aqueous or non-aqueous vehicles, fatty substances of animal or vegetable origin, paraffin derivatives, glycols, the various wetting, dispersing or emulsifying agents, and preservatives.

The invention also has as its subject a process for the preparation of the compounds with the formula (I), characterized in that a compound with the formula (II):

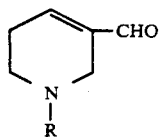
(II)

or one of its salts,
in which R retains the same significance as previously, is submitted to the action of a compound with the formula (III):

NH$_2$OR'$_1$ (III)

or one of its salts,
in which R'$_1$ represents a hydrogen atom or a linear or branched, saturated or unsaturated alkyl radical containing up to 8 carbon atoms in order to obtain the corresponding compound with the formula (I$_A$):

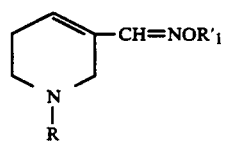
(I$_A$)

which, if required, is salified, or which is submitted, when R'$_1$ represents a hydrogen atom, to the action of a compound with the formula (IV):

R'$_2$Hal (IV)

R'$_2$ representing a radical COalk$_1$ or a radical —(CH$_2$)$_2$N-(alk$_2$)$_2$, alk$_1$ and alk$_2$ being defined as previously and Hal representing a halogen atom, in order to obtain the corresponding compound with the formula (I$_B$):

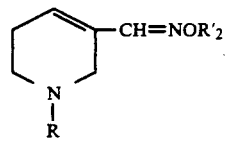
(I$_B$)

which if required is salified, which compound with the formula (I$_A$) in which R'$_1$ does not represent a hydrogen atom, or compound with the formula (I$_B$) is submitted, if required, in the case where R represents a hydrogen atom, to the action of a compound with the formula (VI):

R$_1$Hal (VI)

in which Hal represents a halogen atom and R$_1$ represents a linear, branched or cyclic, saturated or unsaturated alkyl radical, containing up to 8 carbon atoms, possibly substituted by an esterified carboxy radical, or R$_1$ represents an aralkyl radical containing up to 10 carbon atoms, in order to obtain a compound with the formula (I$_C$):

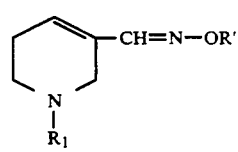
(I$_C$)

in which R$_1$ and R' have the significance indicated previously, which, if required, is salified, or which, if R$_1$ represents an alkyl radical substituted by an esterified carboxy radical, is submitted to the action of a hydrolyzing agent in order to obtain the corresponding compound carrying a free carboxy radical, which compound, if required, is salified.

In a preferred way of carrying out the process of the invention:
  the compound with the formula (II) and the compound with the formula (III) are used in the hydrochloride form,
  in the compounds R'$_2$Hal and R$_1$Hal, represents a chlorine or bromine atom,
  the hydrolysis agent is paratoluene sulphonic acid.

The invention also has as its subject a variant of the preceding process characterized in that a compound with the formula (V):

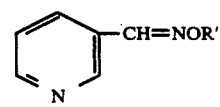
(V)

in which R' retains the same significance as previously, is submitted to the action of a compound with the formula (VI) as previously defined, in order to obtain the compound with the formula (VII):

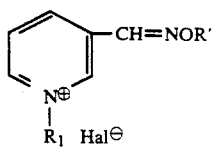

(VII)

which is submitted to the action of a hydrogenation agent, in order to obtain the corresponding compound with the formula (I$_C$):

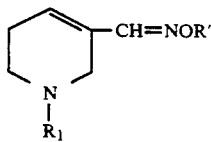

(I$_C$)

in which R$_1$ and R' have the previously indicated significance which, if required, is salified or is submitted, if R$_1$ represents an alkyl radical substituted by an esterified carboxy radical, to the action of a hydrolyzing agent in order to obtain the corresponding compound carrying a free carboxy radical, which compound, if required, is salified.

In a preferred way of carrying out the process, the hydrogenation agent used is sodium hydroboride and the hydrolysis agent is paratoluene sulphonic acid.

The compounds with the formula (II) are products known in a general way, they can be prepared according to the process described in Chem. Ber. 40, 4685, 1907.

The products with the formula (I$_A$) in which R'$_1$ represents a hydrogen atom are known products which can be prepared according to the process described in CHem. Ber. 40, 4712, 1907.

The compounds with the formula (V) are also products known in a general way which can be prepared according to the process described in J.Het. Chem. 1979, 1459.

The examples which follow illustrate the invention without, however, limiting it.

EXAMPLE 1

1-methyl-1,2,5,6-tetrahydropyridin-3-carboxyaldehyde-O-methyloxime hydrochloride

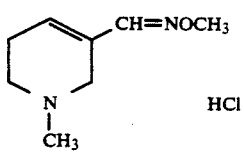

To a solution of 2.74 g (0.017 mol) of 1-methyl-1,2,5,6-tetrahydropyridin-3-carboxaldehyde hydrochloride in 10 cm$^3$ of water, 1.42 g (0.017 mol) of 1-methyl-hydroxylamine hydrochloride is added, with agitation for 2 hours at ambient temperature. The solvent is evaporated, the residue is taken up with acetone, the product is filtered and recrystallized from absolute ethanol. Yield 1.75 g (54%) White crystalline powder. m.p. 228° C. (decomposes).

| Analysis: for C$_8$H$_{14}$N$_2$O.HCl, M.W. 190,681 | | | | | | | |
|---|---|---|---|---|---|---|---|
| Found: | C % | 50.57 | H % | 7.94 | N % | 14.56 |
| Calculated: | | 50.39 | | 7.93 | | 14.69 |

EXAMPLE 2

1-methyl-1,2,5,6-tetrahydropyridin-3-carboxaldehyde-O-ethyloxime hydrochloride

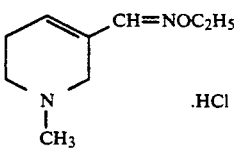

To a solution of 4 g. (0.025 mol) of 1-methyl-1,2,5,6-tetrahydropyridin-3-carboxyaldehyde hydrochloride [Chem.Ber. 40. 4712, 1907/in 15 cm$^3$ of water, 2.42 g (0.025 mol) of O-ethylhydroxylamine hydrochloride is added and the mixture is agitated for 1 hour at ambient temperature, then evaporated to dryness and the residue is crystallized from absolute ethanol. Yield 3.1 g (60.6%). m.p. 197° C. decomposes.

| Analysis: for C$_9$H$_{16}$N$_2$O.HCl, M.W. 204,708 | | | | | | | |
|---|---|---|---|---|---|---|---|
| Found: | C % | 52.61 | H % | 8.47 | N % | 13.47 |
| Calculated: | | 52.80 | | 8.37 | | 13.68 |

EXAMPLE 3

1,2,5,6-tetrahydropyridin-3-carboxaldehyde-O-methyloxime Hydrochloride

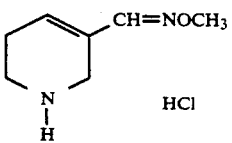

To a solution of 5 g (0.034 mol) of 1,2,5,6-tetrahydropyridin-3-carboxaldehyde hydrochloride, (CHEM. BER. 40, 4685, 1907)— in 30 cm3 of water, 2.85 g (0.034 mol) of O-methyl-hydroxylamine hydrochloride is added with agitation for 1 hour at ambient temperature. The reactional mixture is evaporated to dryness and the residue is recrystallized from absolute ethanol. 4.8 g (80%) of product is obtained with m.p.. 208° C.(decomposes) White crystalline powder.

| Analysis: for C$_7$H$_{12}$N$_2$C$_9$Cl, M.W. 176,654 | | | | | | | |
|---|---|---|---|---|---|---|---|
| Found: | C % | 47.42 | H % | 7.38 | N % | 15.63 |
| Calculated: | | 47.59 | | 7.42 | | 15.86 |

EXAMPLE 4

O-isopropyl-N-methyl-1,2,5,6-tetrahydropyridin-3-carboxaldehyde oxime hydrochloride

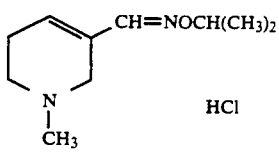

To a solution of 1.24 g (0.0077 mol) of 1-methyl-1,2,5,6-tetrahydropyridin-3-carboxaldehyde hydrochloride in 10 cm$^3$ of water, 0.86 g (0.0077 mol) of O-isopropylhydroxylamine hydrochloride is added with agitation for 1 hour at ambient temperature. The solvent is then evaporated and the residue is re-crystallized from absolute ethanol. Yield, 1 g (59.4%). White crystalline powder with m.p. 234° C. (decomposes).

| Analysis: for $C_{10}H_{18}N_2OHCl$. M.W. 218,735 | | | | | | | |
|---|---|---|---|---|---|---|---|
| Found: | C % | 55.04 | H % | 8.84 | N % | 12.73 |
| Calculated: | | 54.91 | | 8.75 | | 12.81 |

EXAMPLE 5

1-methyl-1,2,5,6-tetrahydropyridin-3-carboxaldehyde-0-acetyl-oxime

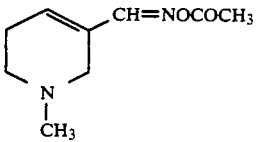

To a solution of 2 g (0.0142 mol) of 1-methyl-1,2,5,6-tetrahydropyridin-3-carboxaldehyde-oxime [Chem. Ber. 40, 4712, (1907) in 20 CM$^3$ of anhydrous THF, 1.44 g (0.0142 mol) of triethylamine and 1.12 g (0.0142 mol) of acetyl chloride are added, with agitation for 1 hour at ambient temperature. The reactional mixture is treated with water, then with an aqueous solution of sodium bicarbonate; the organic phase is separated, dried and the solvent is evaporated. The residue is distilled at 0.05 mm of Hg, collecting the fraction with b.p. 170°–175°. Yield 2.1 g (81%).

| Analysis: $C_9H_{14}N_2O_2$. | | | | | | |
|---|---|---|---|---|---|---|
| Found: | C % | 59.54 | H % | 7.72 | N % | 15.45 |
| Calculated: | | 59.32 | | 7.74 | | 15.37 |

EXAMPLE 6

3-[2-(N,N-dimethylaminoethoxyimino)-methyl]-1-methyl-1,2,5,6-tetrahydropyridine

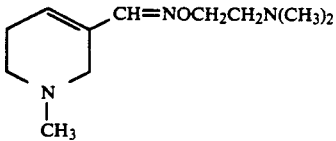

2 g (0.0142 mol) of 1-methyl-1,2,5,6-tetrahydropyridin-3-carboxaldehyde oxime (Chem. Ber. 40, 4712, 1907), and 2.06 g (0.0143 mol) of β-dimethylaminoethylchloride hydrochloride are added to a solution of sodium ethylate (obtained by dissolving 0.66 g (0.0287 mol) of sodium in 40 cm$^3$ of absolute ethanol). The mixture is heated to boiling point for 2 hours, then cooled and the solvent is evaporated to dryness. The residue is taken up with a little 2N NaOH to eliminate any starting oxime still present and extraction is done with ethyl acetate. The organic phase is separated, dried, the solvent is evaporated and the residue is distilled under 0.02 mm of Hg, collecting the fraction with b.p. 100°–105° C., Yellow liquid, yield 2.3 g (76%).

| Analysis: $C_{11}H_{21}N_3O$, HCl, M.W. 211,312 | | | | | | |
|---|---|---|---|---|---|---|
| Found: | C % | 62.21 | H % | 9.84 | N % | 19.84 |
| Calculated: | | 62.52 | | 10.01 | | 19.88 |

EXAMPLE 7

1-ethyl-1,2,5,6-tetrahydro-pyridin-3-carboxaldehyde-O-methyloxime hydrochloride

Stage A:
1-ethyl-3-(methoxyiminomethyl)pyridine iodide.

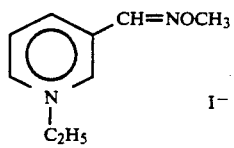

A solution of 10.6 g (0.078 mol) of 3-pyridincarboxaldehyde-O-methyl oxime [J. Het. Chem. (1979) 1459] and 12 g (0.077 mol) of iodoethane in 100 cm$^3$ of acetone is heated for 5 hours to boiling point.

A further 7.8 g (0.05 mol) of iodoethane is added with heating for a further 4 hours at boiling point. The reactional mixture is cooled and the solvent is evaporated. The residue is an oil which solidifies on cooling.

Yield, 16 g (70.2%). m.p. 118° C., decomposes (in acetone); is passed without further purification to the following reaction.

Stage B:
1-ethyl-1,2,5,6-tetrahydro-pyridin-3-carboxaldehyde-O-methyloxime hydrochloride.

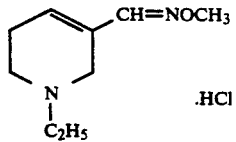

2.5 g (0.066 mol) of sodium borohydride is added to a solution of 10 g (0.034 mol) of 1-ethyl-3-(methoxyiminomethyl)pyridine iodide in 100 cm$^3$ of anhydrous methanol, keeping the temperature at 20°–22° C. with an ice-bath. When the addition is finished, agitation is continued for 1 hour at ambient temperature, then the solvent is evaporated and the residue is taken up with 2N HCl. After alkalizing with solid sodium bicarbonate, extraction is done with ethyl acetate. The organic phase is separated, dried and the solvent is evaporated. The oily residue is taken up with ethyl ether, and filtered on charcoal; HCl gas is bubbled in and the hydrochloride which separates is filtered off and re-crystallized from absolute ethanol. Yield 1.5 g (21.5%). White crystalline powder, m.p. 220° C. (decomposes).

| Analysis: $C_9H_{16}N_2O \cdot HCl$. M.W. 204,708 | | | | | | | |
|---|---|---|---|---|---|---|---|
| Found: | C % | 52.65 | H % | 8.34 | N % | 13.42 |
| Calculated: | | 52.80 | | 8.37 | | 13.68 |

EXAMPLE 8

1-propyl-1,2,5,6-tetrahydropyridin-2-carboxaldehyde-O-methyloxime (in the form of the hydrochloride)

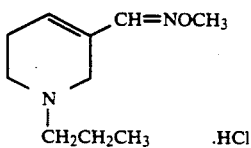

1.74 g ((0.017 mol) of triethylamine and 1.05 g (0.0085 mol) of 1-bromopropane are added to a solution of 1.5 g (0.0085 mol) of 1,2,5,6-tetrahydropyridin-3-carboxaldehyde-O-methyloxime (cf. example 14) in 15 cm³ of DMF. The reactional mixture is heated for 2 hours at 70° C., then cooled and evaporated to dryness. The residue is taken up with water and solid sodium bicarbonate, then extracted with ethyl acetate. The organic phase is separated, dried, and the solvent is evaporated. The residue is chromatographed on a column of silica gel (granulometry 0.04–0.063 mm), eluting with an acetone-ethyl acetate mixture, 1:1. By evaporation of the eluent there remains an oil which is treated with ethereal HCl. The hydro-chloride separates and is recrystallized from absolute ethanol.

Yield 0.9 g (48.4%). White crystalline powder with m.p. 220° C. (decomposes).

| Analysis: $C_{10}H_{18}N_2O$, HCl | | | | | | |
|---|---|---|---|---|---|---|
| Found: | C % | 55.04 | H % | 8.91 | N % | 12.74 |
| Calculated: | | 54.91 | | 8.75 | | 12.81 |

EXAMPLE 9

1-butyl-1,2,5,6-tetrahydropyridin-3-carboxaldehyde-O-methyloxime (in the form of the hydrochloride)

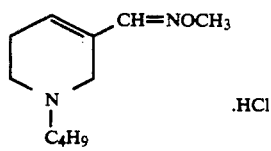

1.26 g (0.0124 mol) of triethylamine and 0.85 g (0.0062 mol) of 1-bromobutane are added to a mixture of 1.1 g (0.0062 mol) of 1,2,5,6-tetrahydropyridin-3-carboxaldehyde-O-methyloxime hydrochloride (cf. example 14) in 15 cm3 of anhydrous DMF, with agitation for 2 hours at ambient temperature. After evaporating to dryness, the residue is taken up with water and anhydrous potassium carbonate, then extracted with ethyl acetate. The organic phase is separated and dried and the solvent is evaporated. The residue is chromatographed on a silica gel column, eluting with a mixture of chloroform and ethanol, 7:3. The eluent is evaporated, the residue is taken up with dry HCl in anhydrous ether, the hydrochloride is filtered off and re-crystallized from absolute ethanol-anhydrous ethyl ether. Yield 0.85 g (59%). White crystalline powder with m.p. 186° C. (decomposes). (at 175° in the Kofler a change is noted in the crystalline form and the melting occurs at 195° C.

| Analysis: $C_{11}H_{20}N_2O$, HCl | | | | | | |
|---|---|---|---|---|---|---|
| Found: | C % | 56.61 | H % | 8.93 | N % | 11.92 |
| Calculated: | | 56.76 | | 9.09 | | 12.04 |

EXAMPLE 10

1-allyl-1,2,5,6-tetrahydropyridin-3-carboxaldehyde-O-methyloxime (in the form of the hydrochloride)

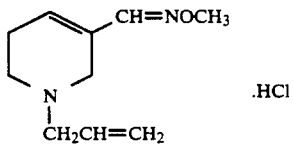

1.38 g (0.01136 mol) of triethylamine and 0.825 g (0.068 mol) of freshly distilled allyl bromide are added to a solution of 1.2 g (0.0068 mol) of 1,2,5,6-tetrahydropyridin-3-carboxaldehyde-O-methyloxime (cf. example 14) in 15 cm³ of anhydrous DMF. The reactional mixture is agitated for 2 hours at ambient temperature, then evaporated to dryness. The residue is taken up with water and potassium carbonate, then extracted with ethyl acetate. The organic phase is separated and dried and the solvent is evaporated off. The residue is dissolved in anhydrous ethyl ether, filtered on charcoal and treated with HCl gas. The hydrochloride which separates is filtered off and re-crystallized from absolute ethanol.

Yield, 1.2 g (81.4%). White crystalline powder with m.p. 220° C. (decomposes). The sample for analysis is re-crystallized from absolute ethanol, m.p. 221° C., (decomposes).

| Analysis: $C_{10}H_{16}N_2O$. HCl M.W. 190,681 | | | | | | |
|---|---|---|---|---|---|---|
| Found: | C % | 55.02 | H % | 7.72 | N % | 12.74 |
| Calculated: | | 55.42 | | 7.91 | | 12.93 |

EXAMPLE 11

1-pentyl-1,2,5,6-tetrahydropyridin-3-carboxaldehyde-O-methyloxime (in the hydrochloride form)

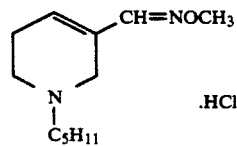

1.72 g (0.017 mol) of triethylamine and 1.28 g (0.0085 mol) of 1-bromopentane are added to a mixture of 1.5 g (0.0085 mol) of 1,2,5,6-tetrahydropyridin-3-carboxaldehyde-O-methyloxime hydrochloride (cf. example 14 in 20 cm³ of DMF, and the whole is agitated for 3 hours at ambient temperature. The solvent is evaporated to dryness, the residue is taken up with a little water and extracted with ethyl acetate. The organic phase is separated and dried and the solvent is evaporated. The residue is taken up with anhydrous ethyl ether and the solution is treated with gaseous HCl. The hydrochloride which separates is filtered off and re-crystallized from a mixture of absolute ethanol and anhydrous ethyl ether.

Yield, 1.1 g (52.4%). White crystalline powder with m.p. 185° C., (decomposes). Unchanged even after a further crystallization from the same mixture of solvents. In the Kofler a change in the crystalline form is noted at 140° C., and complete fusion at 191° C.

| Analysis: $C_{12}H_{22}N_2O.HCl$. M.W. 190,681 | | | | | | | |
|---|---|---|---|---|---|---|---|
| Found: | C % | 58.27 | H % | 9.48 | N % | 11.19 |
| Calculated: | | 58.40 | | 9.39 | | 11.35 |

EXAMPLE 12

1-methyl-1,2,5,6-tetrahydropyridin-3-carboxaldehyde-O-propargyloxime (in the form of the hydrochloride)

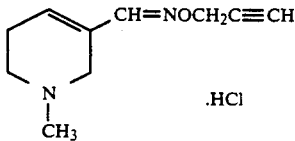

1.23 g (0.00114 mol) of O-propargylhydroxylamine hydrochloride is added to a solution of 1.84 g (0.0114 mol) of 1-methyl-1,2,5,6-tetrahydropyridin-3-carboxaldehyde hydrochloride in 15 cm³ of water, with agitation for 1 hour at ambient temperature. The reactional mixture is evaporated to dryness and the residue is crystallized from absolute ethanol. Yield 2.2 g (about 90%).

White crystalline powder with m.p. 157° C. (decomposes).

| Analysis: $C_{10}H_{14}N_2O.HCl$. M.W. 190,681 | | | | | | | |
|---|---|---|---|---|---|---|---|
| Found: | C % | 55.81 | H % | 6.95 | N % | 13.11 |
| Calculated: | | 55.94 | | 7.04 | | 13.05. |

EXAMPLE 13

1-benzyl-1,2,5,6-tetrahydropyridin-3-carboxaldehyde-O-methyloxime

Stage A: 1-benzyl-3-carboxaldehyde-O-methyloxime pyridinium bromide.

22 g of 3-aldoxime pyridine-O-methylether (J.Hec.-Chem.1979, p.1459) is dissolved in anhydrous ethanol, 40.2 g of benzyl bromide is added and the whole is heated for 12 hours at reflux. The solvent is eliminated under reduced pressure, the residue is taken up with a mixture of ethanol and anhydrous ether, and after filtering, 39.5 g of the expected product is obtained. m.p. 103°-106° C.

Stage B: 1-benzyl-1,2,5,6-tetrahydropyridin-3-carboxaldehyde-O-methyloxime, hydrochloride.

30 g of the product obtained above is dissolved in 250 cm³ of anhydrous methanol, cooled to 5°-10° C., and 4.8 g of sodium borohydride is added in small fractions, while the temperature is maintained at 5°-10° C. The mixture is agitated for 2 hours at ambient temperature, then the solvent is eliminated at 40° C. under reduced pressure. The residue is chromatographed on silica, eluting with a mixture of ethyl acetate and toluene (6-4) and 13 g of product in basic form is obtained (b.p. 230° C. under 0.05 mm Hg) which is converted into the hydrochloride. m.p. 261° C. (decomposes), after crystallization from 95% ethanol.

| Analysis: $C_{14}H_{18}N_2O$, HCl: 266.775 | | | | | | | |
|---|---|---|---|---|---|---|---|
| Calculated: | C % | 63.03 | H % | 7.18 | N % | 10.50 |
| Found: | | 62.88 | | 7.31 | | 10.24 |

EXAMPLE 14

1-cyclopropyl methyl-1,2,5,6-tetrahydropyridin-3-carboxaldehyde-O-methyloxime, hydrochloride 0.9 g of chloromethylcyclopropane is added to 2.8 g of 1,2,5,6-tetrahydropyridin-3-carboxaldehyde O-methyloxime and after heating for 3 hours, 0.45 g of chloromethylcyclopropane is added and the temperature is maintained at 80° C. for 6 hours. The mixture is then cooled, diluted in anhydrous ethyl ether and filtered. The filtrate is chromatographed on silica, eluting with ethyl acetate. After elimination of the solvent, 1.4 g of an oil is obtained which is distilled at 130° C. under 0.1 mm Hg., then acidified with gaseous hydrochloric acid in anhydrous ethyl ether, and crystallized from a mixture of ethanol and ethyl ether. m.p. 233° C. (decomposes).

| Analysis: $C_{11}H_{18}N_2O$, HCl: 230.745 | | | | | | | |
|---|---|---|---|---|---|---|---|
| Calculated: | C % | 57.25 | H % | 8.30 | N % | 12.14 |
| Found: | | 57.03 | | 8.17 | | 11.96. |

Preparation of 1,2,5,6-tetrahydropyridin-3-carboxaldehyde O-methyloxime used as starting product.

Stage A: 1-alpha-chloroethoxycarbonyl-1,2,5,6-tetrahydropyridin-3-carboxaldehyde-O-methyloxime.

A solution of 13.2 g of 1-benzyl-1,2,5,6-tetrahydropyridin-3-carboxaldehyde-O-methyloxime in 120 cm³ of anhydrous 1,2-dichloroethane is cooled to 0° C., 11.7 g of alpha-chloroethyl-chloroformate is added and the whole is heated to reflux for 2 hours. After cooling, the insoluble matter is filtered off. The filtrate is evaporated to dryness, and the residue is taken up with anhydrous ether, diluted and filtered. The filtrate is evaporated and 19.8 g of product is obtained which is used immediately for the following reaction.

Stage B: 1,2,5,6-tetrahydropyridin-3-carboxaldehyde-O-methyloxime.

19 g of the product obtained above is dissolved in 100 cm³ of anhydrous methanol and heated to 50° C. for 1 hour. The solvent is evaporated to dryness, and the residue is taken up in anhydrous ethyl ether, agitated, filtered, and 8.4 g of the expected product is obtained.

EXAMPLE 15

1,1-dimethyl ethoxycarbonylmethyl-1,2,5,6-tetrahydropyridin-3-carboxaldehyde-O-methyloxime hydrochloride 4.5 g of 1,2,5,6-tetrahydropyridin-3-carboxaldehyde-O-methyloxime prepared as in example 14 is dissolved in 30 cm³ of anhydrous benzene; 3.25 g of triethylamine is added and then 6.3 g of tributyl bromoacetate is added slowly. After 30 minutes of reaction, the triethylamine chloride formed is filtered off, the benzene is evaporated, and the remainder is distilled at 130° C. under 1 mm Hg., and 6 g of an oily product is obtained. The hydrochloride is prepared with gaseous hydrochloric acid in anhydrous ethyl ether, and is re-crystallized from a mixture of ethanol and anhydrous ether. m.p. 182° C., (decomposes).

| Analysis: $C_{13}H_{22}N_2O_3$, HCl. M.W. 290.797 | | | | | | | |
|---|---|---|---|---|---|---|---|
| Calculated: | C % | 53.69 | H % | 7.97 | N % | 9.63 |
| Found: | | 53.87 | | 8.03 | | 9.81 |

EXAMPLE 16

1-carboxymethyl-1,2,5,6-tetrahydropyridin-3-carboxaldehyde-O-methyloxime hydrochloride 3 g of 1-(1,1-dimethylethoxycarbonylmethyl)-1,2,5,6-tetrahydropyridin-3-carboxaldehyde-O-methyloxime is dissolved in 30 cm³ of anhydrous toluene, 2.27 g of paratoluene sulphonic acid is added and the whole is heated to reflux for 1 hour. After evaporating to dryness, the residue is taken up with 1,2-dichloroethane, salified with gaseous hydrochloric acid, and precipitated with anhydrous ethyl ether. By filtering and re-crystallizing from ethanol, 1.8 g of the expected product is obtained. m.p. 213° C., with decomposition).

| Analysis: $C_9H_{14}N_2O_3$ HCl: 234.692 | | | | | | | |
|---|---|---|---|---|---|---|---|
| Calculated: | C % | 46.06 | H % | 6.44 | N % | 11.94 |
| Found: | | 45.92 | | 6.27 | | 11.91 |

EXAMPLE 17

1-(but-2-enyl)-1,2,5,6-tetrahydropyridin-3-carboxaldehyde-O-methyloxime hydrochloride The operation is done as in example 15 in dimethylformamide with crotyl bromide22 agitating for 1 hour at ambient temperature. The dry residue is taken up with a little water and extracted with ethyl acetate. The hydrochloride obtained melts at 215° C. (decomposes).

| Analysis: $C_{11}H_{18}N_2O.HCl$. M.W. 230.745 | | | | | | | |
|---|---|---|---|---|---|---|---|
| Calculated: | C % | 57.26 | H % | 7.86 | N % | 12.14 |
| Found: | | 57.02 | | 8.06 | | 12.07 |

EXAMPLE 18

1-(prop-2-yl)-1,2,5,6-tetrahydropyridin-3-carboxaldehyde-O-methyloxime hydrochloride 3.2 g of 1,2,5,6-tetrahydropyridin-3-carboxaldehyde-O-methyloxime is heated to reflux for 1 hour with 1.41 g of 2-bromopropane. After alkalizing with a 10% aqueous solution of potassium carbonate, extraction is done with ethyl acetate, and the extracts are evaporated to dryness. The residue is chromatographed on silica, eluting with a mixture of methanol and chloroform (2-8). 1.2 g of an oil is obtained which is distilled at 110° C. under 0.08 mm Hg, and is then acidified with gaseous hydrochloric acid in ether. After re-crystallization from isopropyl alcohol-ethyl ether, the hydrochloride melts at 210° C., with decomposition.

| Analysis: $C_{10}H_{18}N_2O$, HCl: 218.728 | | | | | | | |
|---|---|---|---|---|---|---|---|
| Calculated: | C % | 54.91 | H % | 8.76 | N % | 12.81 |
| Found: | | 54.68 | | 8.72 | | 12.71 |

EXAMPLE 19

1-(prop-2-ynyl)-1,2,5,6-tetrahydropyridin-3-carboxaldehyde-O-methyloxime hydrochloride The operation is done as in example 17, using propynyl bromide and the expected hydrochloride is obtained. m.p. 229° C., (decomposes).

| Analysis: $C_{10}H_{14}N_2O$. HCl: 214.696 | | | | | | | |
|---|---|---|---|---|---|---|---|
| Calculated: | C % | 55.94 | H % | 7.04 | N % | 13.05 |
| Found: | | 56.02 | | 7.07 | | 12.88 |

EXAMPLE 20

1-cyclopentyl-1,2,5,6-tetrahydropyridin-3-carboxaldehyde-O-methyloxime hydrochloride The operation is done as in example 18, using cyclopentyl bromide while heating at 60° C. for 8 hours, and the expected product is obtained. m.p. 213° C.

| Analysis: $C_{12}H_{20}N_2O$, HCl: 244.766 | | | | | | | |
|---|---|---|---|---|---|---|---|
| Calculated: | C % | 58.89 | H % | 8.65 | N % | 11.45 |
| Found: | | 58.62 | | 8.49 | | 11.38 |

EXAMPLE 21

1,2,5,6-tetrahydropyridin-3-carboxaldehyde-O-propargyloxime hydrochloride

The operation is done as in example 12, starting with 1.47 g of 1,2,5,6-tetrahydropyridin-3-carboxaldehyde hydrochloride (Chem.Ber. 40, 4685 (1907) and 1.07 g of O-propargylhydroxylaminehydrochloride (U.S. Pat. No. 3,398,180). 1.2 g of the expected product is obtained. m.p. 202° C.

| Analysis: $C_9H_{12}N_2O$, HCl: 200.676 | | | | | | | |
|---|---|---|---|---|---|---|---|
| Calculated: | C % | 53.87 | H % | 6.5 | N % | 14.12 |
| Found: | | 53.64 | | 6.53 | | 13.96 |

EXAMPLE 22

1-methyl-1,2,5,6-tetrahydropyridin-3-carboxaldehyde-O-allyloxime hydrochloride 2.7 g of N-methyl-1,2,5,6-tetrahydropyridin-3-aldoxime (J.Pharm. Sciences 56 (9), 1190, 1967) is added to a solution of 0.5 g of sodium in 20 cm³ of anhydrous ethanol, then 1.67 cm³ of allyl bromide is added slowly. The mixture is heated to reflux for 3 hours, then poured into 60 cm³ of water, and extracted with methylene chloride. The organic phase is washed with salted water, dried and concentrated to dryness. The residue is chromatographed on silica, eluting with a mixture of ethyl acetate and methanol (95-5). 1 g of an oil is obtained which distills at 125°-130° C. under 5 mm Hg. This oil is dissolved in anhydrous ether, and salified with gaseous hydrochloric acid. The hydrochloride obtained is recrystallized from a mixture of methanol and ethyl ether. m.p. 168°–169° C. (decomposes).

| Analysis: $C_{10}H_{16}N_2O$, HCl: 216,712 | | | | | | | |
|---|---|---|---|---|---|---|---|
| Calculated: | C % | 55.42 | H % | 7.91 | N % | 12.93 |
| Found: | | 55.14 | | 7.82 | | 12.76 |

EXAMPLE 23

1-methyl-1,2,5,6-tetrahydropyridin-3-carboxaldehyde-O-buten-2-yloxime hydrochloride The operation is done as in example 22, starting with 3.5 cm$^3$ of crotyl bromide and 3.8 g of 1-methyl-1,2,5,6-tetrahydropyridin-3-aldoxime, heating 4 hours at reflux. 1.78 g of an oil is obtained which distills at 160°–165° under 3 mm Hg. The hydrochloride is prepared which melts at 164°–165° C., with decomposition.

| Analysis: $C_{11}H_{18}N_2O$, HCl: 230.739 | | | | | | | |
|---|---|---|---|---|---|---|---|
| Calculated: | C % | 57.26 | H % | 8.30 | N % | 12.14 |
| Found: | | 54.04 | | 8.28 | | 11.99 |

Acute Toxicity

Male rats (CD$_1$ Charles Rivers) were used, weighing 22 to 24 g, fasting for 16 hours. The products were administered by oral route at doses of 1000, 500, 250, 125, 62, 31 and 16 mg/Kg. The mortality was checked in the seven days following the treatment.

| Example No. | LD$_{50}$, mg/Kg |
|---|---|
| 1 | 450 |
| 2 | 250 |
| 3 | 75 |
| 4 | 350 |
| 5 | 500 |
| 6 | 750 |
| 8 | 100 |
| 9 | 30 |
| 10 | 175 |
| 11 | 175 |
| 12 | 60 |
| Arecoline HBr | 600 |

ILEUM FROM GUINEA-PIGS

Sections of ileum were removed from guinea-pigs killed by decapitation. The isolated ileum was suspended in a bath containing 10 ml of Tyrode's solution thermo-regulated at 37° C. and aerated with a mixture of O$_2$ (95%) and CO$_2$ (5%). The contracting effect of the compounds was detected, with an isometric transducer connected to a recorder. The products under test were added at scalar concentrations between $1 \times 10^{-3}$ and $1 \times 10^{-8}$ moles.

The products endowed with contracting activity were checked against atropine or hexamethonium to establish whether the activity was of muscarine type or nicotine type. The possible antagonist activity of the products was tested against acetylcholine.

The agonist activity was expressed in pD$_2$ (negative logarithm of the dose which produces 50% of the maximum effect.)

The antagonist activity was expressed as ED$_{50}$ (dose inhibiting 50% of the maximum response induced with acetylcholine.

| Example N°. | pD$_2$ | ED$_{50}$ |
|---|---|---|
| 1 | 6.28 | — |
| 2 | <3 | $1.8 \times 10^{-4}$ |
| 3 | 6.58 | — |
| 4 | <3 | $1.1 \times 10^{-5}$ |
| 5 | 4.29 | — |
| 6 | 3.83 | — |
| 7 | <3 | $2.0 \times 10^{-4}$ |
| 8 | 4.60 | — |
| 9 | <3 | $2.3 \times 10^{-4}$ |
| 10 | 4.80 | — |
| 11 | <3 | $1.6 \times 10^{-4}$ |
| 12 | 6.32 | — |
| Arecoline | 6.48 | — |

Diarrhoea activity

Male rats (CD$_1$ Charles Rivers) were used, weighing 25–30 g, fasting for 6 hours. The compounds were administered by oral route, by means of an oesophagic probe, dissolved at 0.5% in methocel. The controls received only the vehicle (20 ml/Kg).

After the treatment, the animals were put separately in cages having the base covered with blotting paper, and were observed 30′, 60′, 120′ and 180′ after the treatment. The sheet of absorbent paper was changed after every observation. In accordance with the method of Randall and Baruth (Arch. Int. Pharmacodyn. 220, 94, 1976) the consistency of the faeces is evaluated arbitrarily according to the following scale of values:

0: solid consistency
1: faeces moderately soft with or without formation of a halo of humidity
2: faeces moderately soft with formation of a well defined circle of humidity,
3: faeces soft, with formation of a large circle of humidity,
4: faeces without consistency with formation of a very large circle of humidity.

For each compound, the dose was evaluated which induced diarrhoea in 50% of the animals, according to the method of Miller and Tainter, (Proc. Soc. Exp. Biol. Med. 57, 261, 1944)

| Example N°. | ED$_{50}$ mg/Kg |
|---|---|
| 1 | 0.6 |
| 2 | 50 |
| 3 | 0.15 |
| 4 | >100 |
| 5 | >100 |
| 6 | >100 |
| 7 | 10 |
| 8 | 1.7 |
| 9 | 3.5 |
| 10 | 1.2 |
| 11 | 5 |
| 12 | 5.5 |
| Arecoline.HBr | 35 |

HYPOTHERMIC ACTIVITY

Male mice (CD$_1$ Charles Rivers) were used, weighing 25–30 g, fasting for 6 hours. The body temperature was noted by means of a thermo-couple, inserted in the rectum for about 1.5 cm and connected to an electric temperature indicator. The compounds were administered by oral or subcutaneous route and the values of the body temperature were observed at time 0 and at 30′, 60′, 120′ and 180′ after the treatment.

The degree of hypothermia was evaluated as the difference between the treated and the control animals, and the dose was determined which was necessary to reduce the body temperature by 1° C.

Example No. Effective dose (−1° C.) in mg/kg.

| | oral | sub-cutaneous. |
|---|---|---|
| 1 | 0.46 | 0.14 |
| 2 | 13 | 11 |
| 3 | 0.11 | 0.12 |
| 4 | 40 | — |
| 5 | 39 | — |
| 6 | 135 | — |
| 7 | 0.97 | 1.16 |
| 8 | 0.34 | 0.83 |
| 9 | 0.79 | 0.85 |
| 10 | 0.34 | 0.86 |
| 11 | 3 | 4 |
| 12 | 2 | 0.63 |
| Arecoline.HBr | 194 | 3 |

The duration of action of the products was evaluated using doses of equal ability to cause a reduction of body temperature of 1°–1,5° C.

| VARIATIONS OF THE BODY TEMPERATURE | | | | | | |
|---|---|---|---|---|---|---|
| | dose | admin. | time in minutes after the treatment | | | |
| | mg/kg | route | 0 | 30 | 60 | 120 | 180 |
| Example | 0,15 | os | +0.1 | −1,5** | −0,8** | −0,2 | ±0 |
| 3 | 0,15 | sc | ±0 | −1,2** | −0,8** | −0,2 | −0,1 |
| Example | 1,25 | os | ±0 | −1,1** | −1,1** | −0,6** | −0,2 |
| 7 | 1,25 | sc | ±0 | −0,5** | −1,0** | −0,6** | −0,1 |
| Example | 0,5 | os | ±0 | −1,5** | −1,3** | −0,4** | ±0 |
| 8 | 1 | sc | ±0 | −0,7** | −1,2** | −0,2 | −0,1 |
| Example | 0,5 | os | −0,1 | −1,5** | −0,7** | −0,1 | +0,2 |
| 10 | 0,75 | sc | ±0 | −0,8** | −1,0** | −0,1 | +0,1 |
| arecolina | 200 | os | +0,1 | −1,1** | −1,0** | −0,2 | −0,1 |
| HBr | 3,5 | sc | −0,1 | −1,5** | −0,1 | +0,2 | +0,2 |

**Values significantly different from the controls. (p < 0,01)

We claim:

1. A compound of the formula (I):

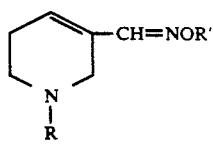

(I)

in which R represents a hydrogen atom, a linear, branched or cyclic alkyl, alkenyl, alkynyl radical containing up to 8 carbon atoms, possibly substituted by a free or esterified carboxy radical, said esterified carboxyl radical being alkoxycarbonyl in which the alkoxy radical includes up to 8 carbon atoms, or R represents a benzyl or phenethyl radical and R' represents a linear or branched, alkyl, alkenyl or alkynyl radical, containing up to 8 carbon atoms, a radical —COalk$_1$ or a radical —(CH$_2$)$_2$N(alk$_2$)$_2$, alk$_1$ and alk$_2$ representing an alkyl radical containing up to 8 carbon atoms, as well as their addition salts with pharmaceutically acceptable acids.

2. The compounds with the formula (I) as defined in claim 1, in which R represents a hydrogen atom, as well as their addition salts with acids.

3. The compounds of the formula (I) as defined in claim 1, in which R represents an alkyl, alkenyl or alkynyl radical containing from 1 to 4 carbon atoms, as well as their addition salts with acids.

4. The compounds of the formula (I) as defined in claim 3, in which R represents a methyl, ethyl, propyl or allyl radical, as well as their addition salts with acids.

5. The compounds of the formula (I) as defined in any of claim 1 to 4, in which R' represents a methyl radical, as well as their additions salts with acids.

6. A compound of the formula as defined in claim 1, selected from the group consisting of
   1-methyl-1,2,5,6-tetrahydropyridin-3-carboxal dehyde-O-Methyl oxime;
   1-ethyl-1,2,5,6-tetrahydropyridin-3-carboxal dehyde-O-Methyl oxime;
   1,2,5,6-tetrahydropyridin-3-carboxal dehyde-O-methyl oxime;
   1-propyl-1,2,5,6-tetrahydropyridin-3-carboxal dehyde-O-methyl oxime; and
   1-allyl-1,2,5,6-tetrahydropyridin-3-carboxal dehyde-O-methyl oxime;
as well as its salt with an acid.

7. The hydrochlorides of a compound according to claim 6.

8. A pharmaceutical composition for the treatment of Alzheimer's disease, senile dementia, or memory disorders in the aged, susceptible to treatment with cholinergics or muscarinic agents, comprising administering to the patient a cholinomimetically effective amount of a compound as defined in claim 1 as well as its salts with a pharmaceutically acceptable acid and a pharmaceutically acceptable carrier.

9. A method for treating patients suffering from Alzheimer's disease, senile dementia, or memory disorders in the aged, susceptible to treatment with cholinergics or muscarinic agents, comprising administering to the patient a cholinomimetically effective amount of a compound as defined in any one of claims 1 to 6, or its salt with a pharmaceutically acceptable acid.

10. A compound selected from the group consisting of 1-methyl-1,2,5,6-tetrahydropyridin-3-carboxaldehyde-O-methyl oxime; 1-ethyl-1,2,5,6-tetrahydropyridin-3-carboxaldehyde-O-methyl oxime; and 1,2,5,6-tetrahydropyridin-3-carboxaldehyde-O-methyl oxime; and its salts with a pharmaceutically acceptable acid.

11. A compound selected from the group consisting of 1-methyl-1,2,5,6-tetrahydropyridin-3-carboxyaldehyde-O-methyl oxime, and its salts with a pharmaceutically acceptable acid.

12. A compound selected from the group consisting of 1-ethyl-1,2,5,6-tetrahydropyridin-3-carboxaldehyde-O-methyl oxime, and its salts with a pharmaceutically acceptable acid.

13. A compound selected from the group consisting of 1,2,5,6-tetrahydropyridin-3-carboxaldehyde-O-methyl oxime, and its salts with a pharmaceutically acceptable acid.

14. The hydrochlorides of a compound according to claim 10.

* * * * *